(12) United States Patent
McQueen et al.

(10) Patent No.: US 7,192,449 B1
(45) Date of Patent: *Mar. 20, 2007

(54) CONSTRAINED ACETABULAR INSERT FOR TOTAL HIP ARTHROPLASTY

(75) Inventors: David A. McQueen, Kechl, KS (US); Christoph A. Roth, Wichita, KS (US)

(73) Assignee: Orthopaedic Research Institute, Inc., Wichita, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/239,870

(22) Filed: Jan. 29, 1999

(51) Int. Cl.
*A61F 2/32* (2006.01)
(52) U.S. Cl. .................................. 623/22.25
(58) Field of Classification Search ..... 623/22.17–22.2
See application file for complete search history.

(56) References Cited

U.S. PATENT DOCUMENTS 4,676,798 A * 6/1987 Noiles ...................... 623/22.18
4,960,427 A * 10/1990 Noiles ...................... 623/22.18

* cited by examiner

Primary Examiner—Corrine McDermott
Assistant Examiner—Christopher D Prone
(74) Attorney, Agent, or Firm—Hovey Williams LLP

(57) ABSTRACT

A hip prosthesis (20) having a shell (22), liner (24), and retainer ring (26) is utilized for hip arthroplasty. The liner (24) fits inside the shell (22), which is attached to a patient's pelvis, and the retainer ring (26) engages a terminal liner margin (54) to inhibit expansion of and decrease the size of a restricted liner opening (72) defined by the liner margin (54). By inhibiting expansion of the liner opening (72), the ball (92) of a patient's femur (90) is securely held in the liner (24). In one embodiment, the liner (98) is inhibited from rotation relative to the shell (96) by a plurality of protrusions (106) which mate with recesses (102) in the shell (96). In that embodiment, the liner (98) is provided with catch lips (108) to hold the liner (98) in the shell (96) and a positioning flange (110) which operates to form a relief gap (120) between the shell (96) and the liner (98). In another embodiment, the retainer ring comprises an attachment portion (128) and a retainer portion (130) with a threaded connection (132) between the attachment portion (128) and the retainer portion (130).

21 Claims, 4 Drawing Sheets

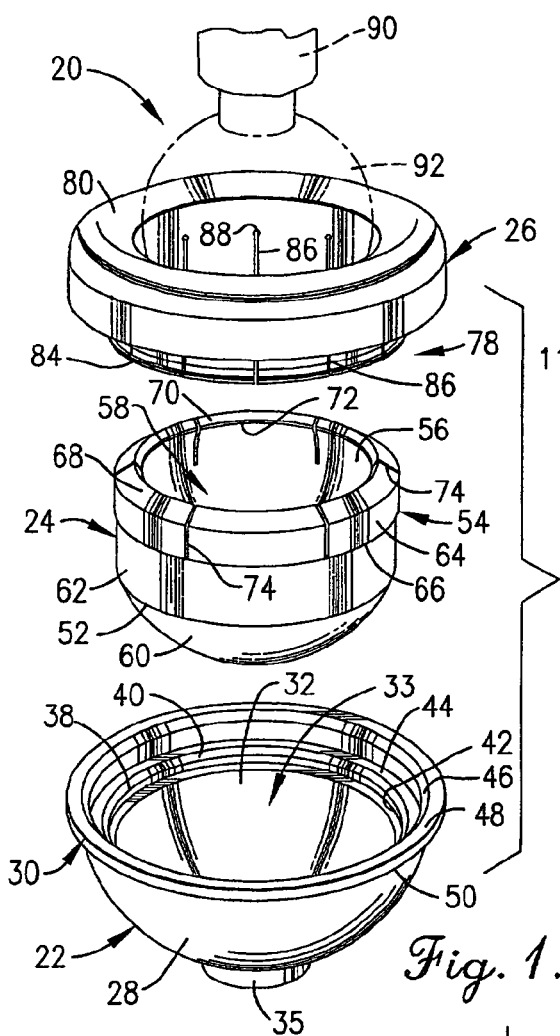
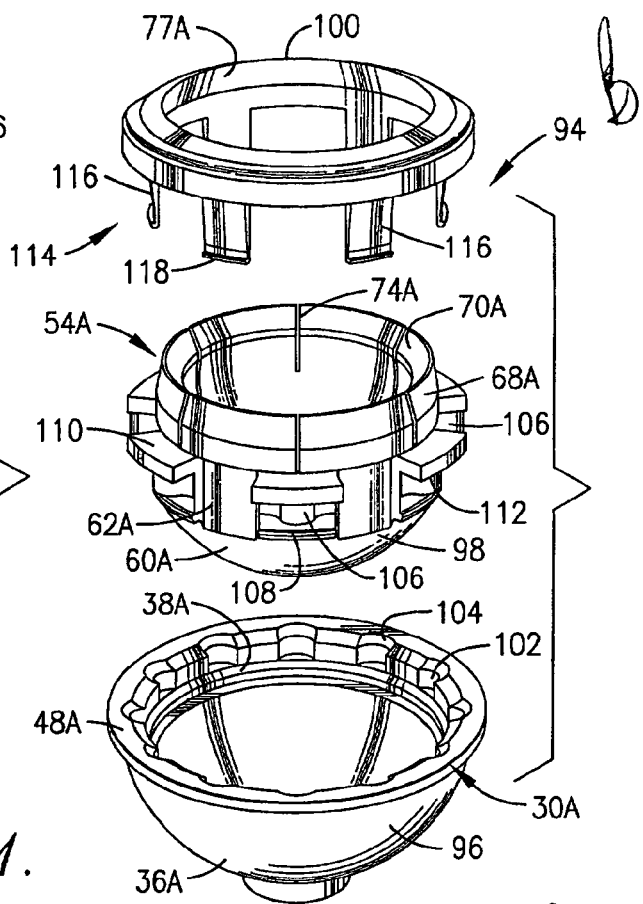
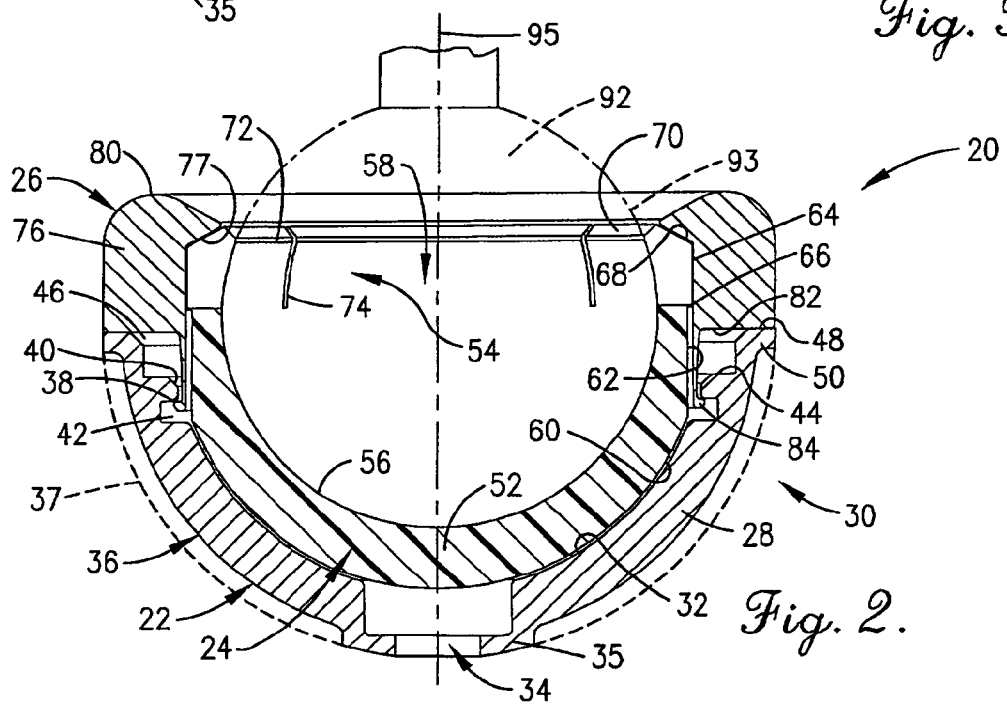
Fig. 1.
Fig. 3.
Fig. 2.

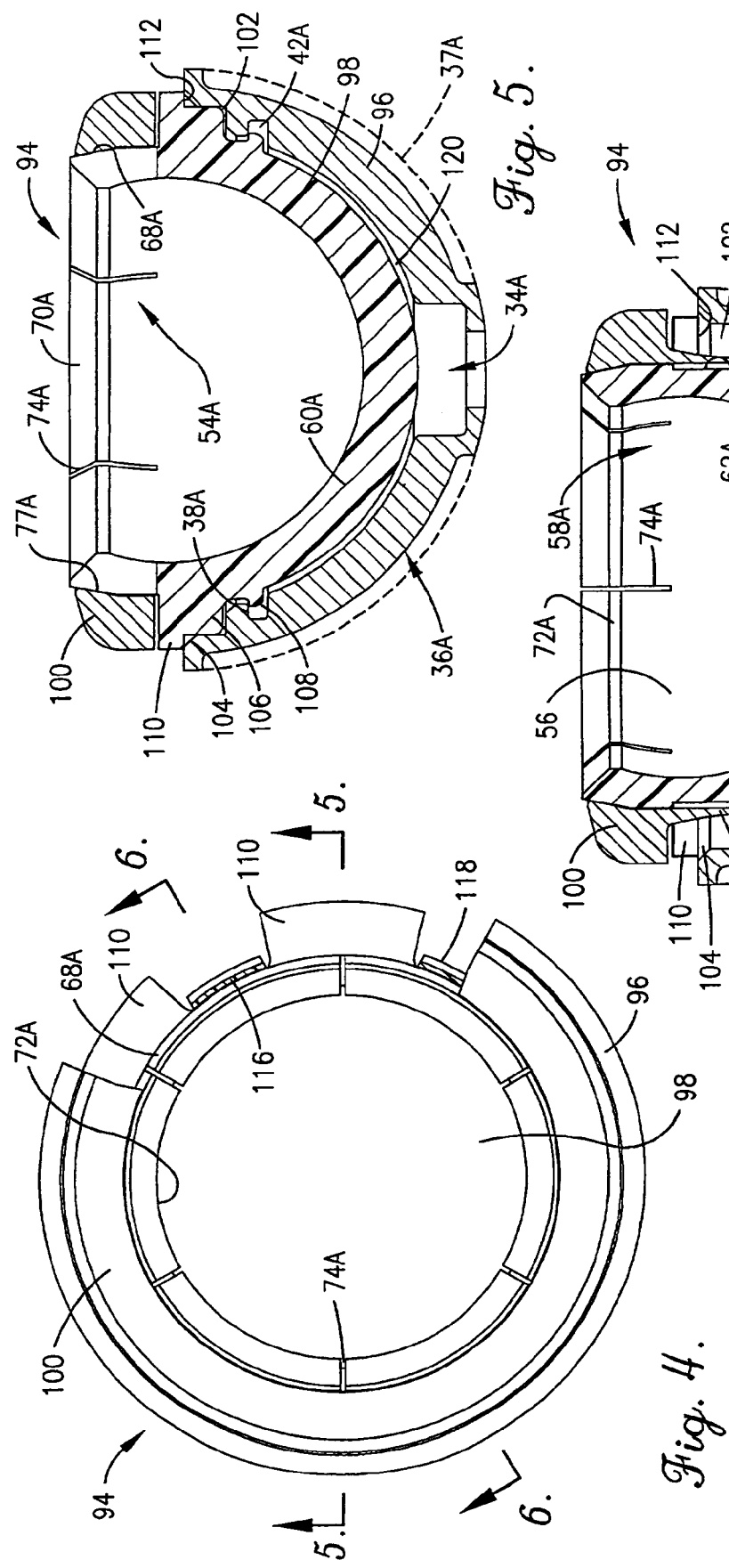
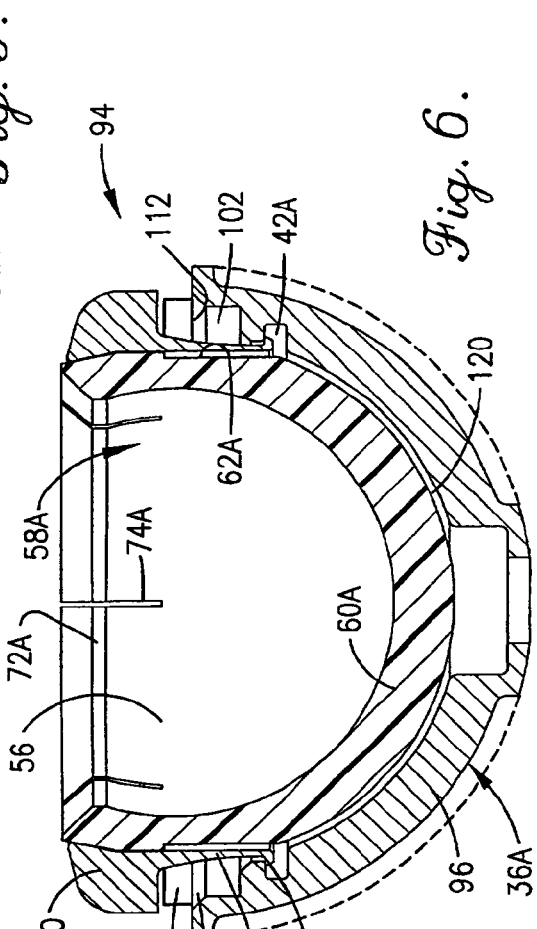

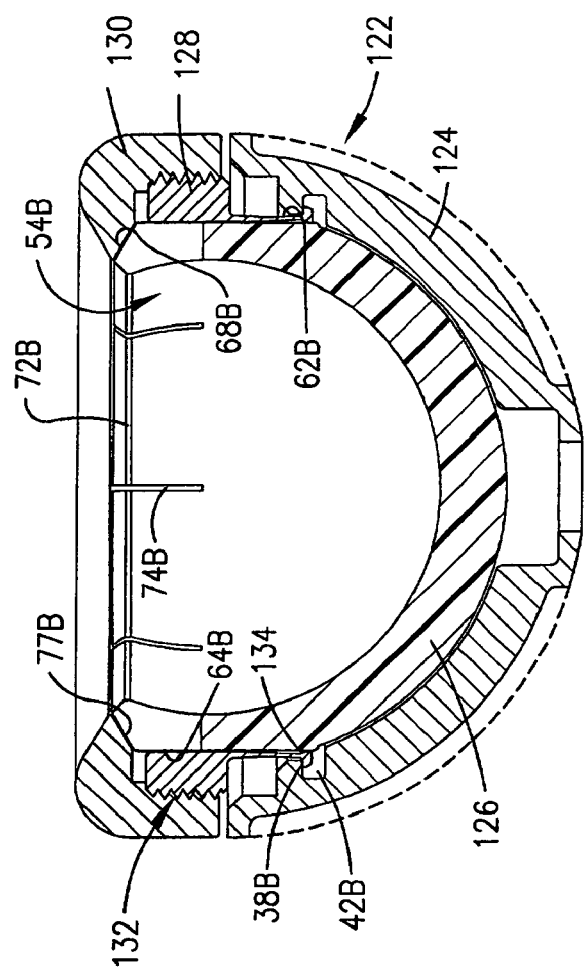
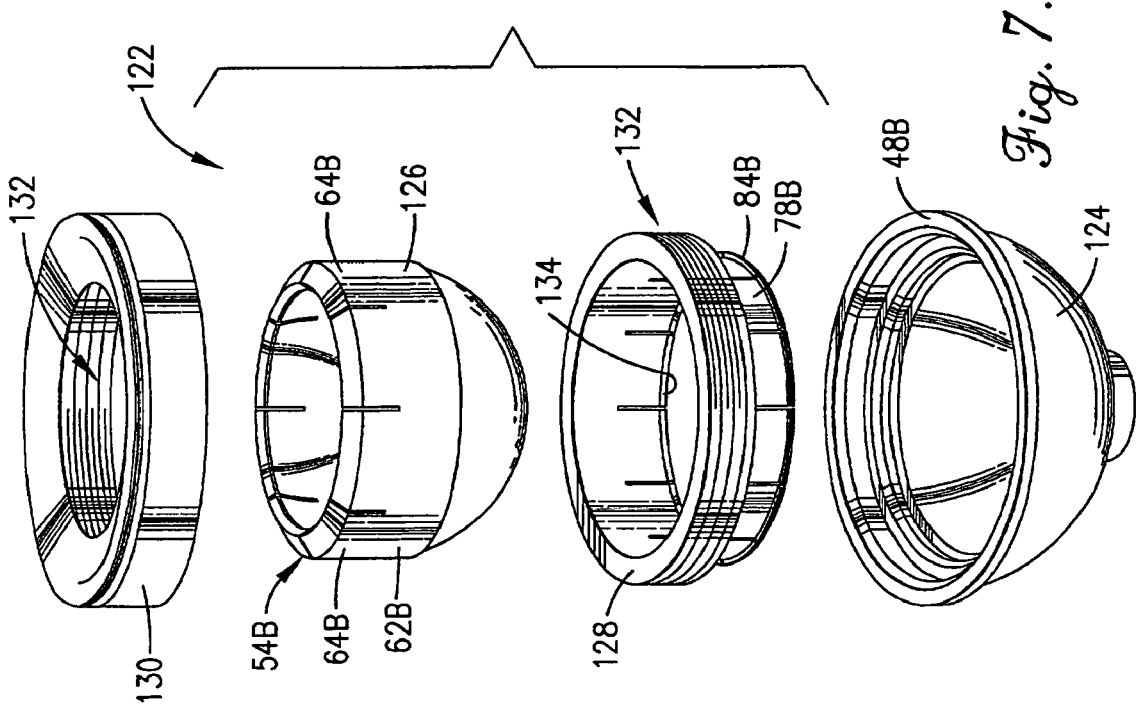

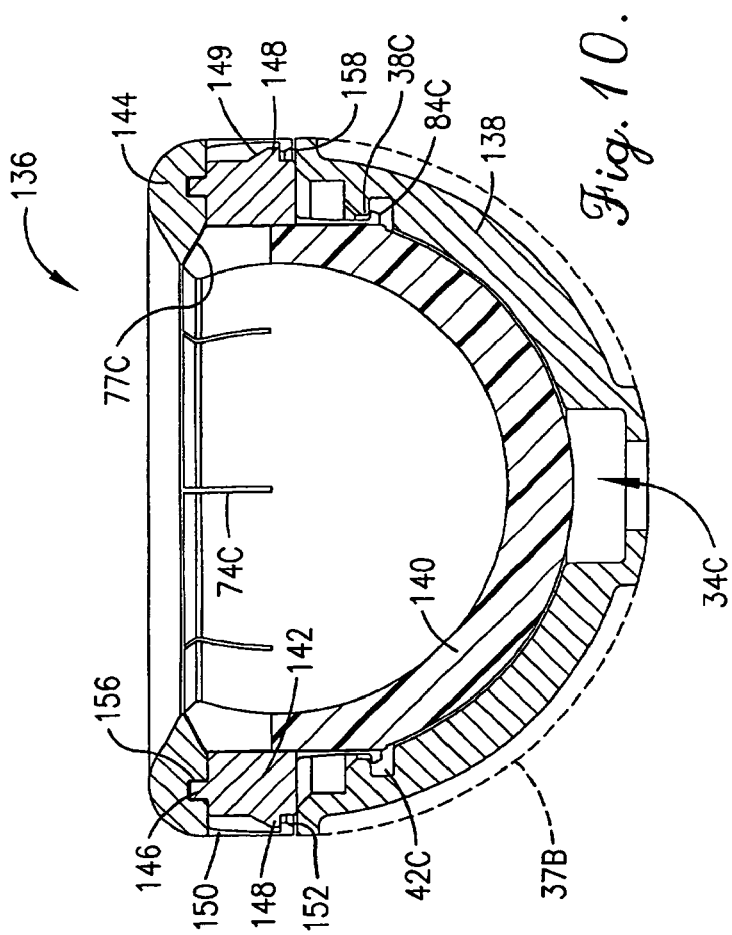
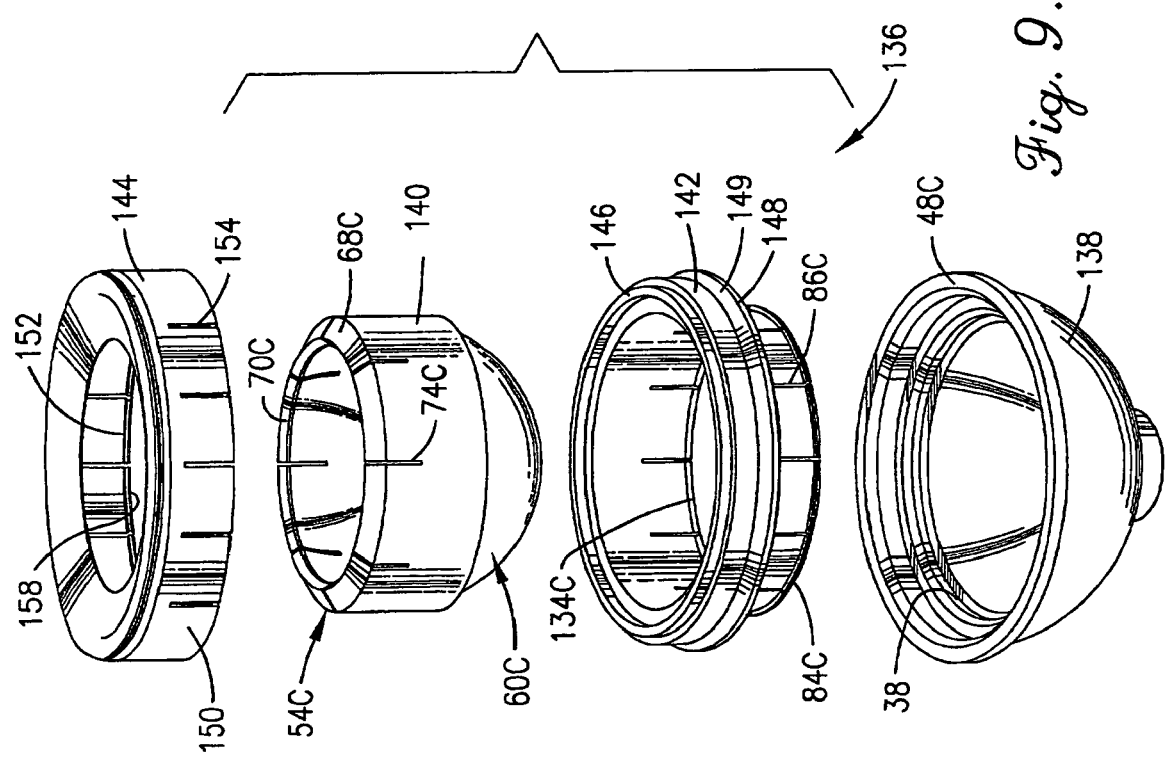

CONSTRAINED ACETABULAR INSERT FOR TOTAL HIP ARTHROPLASTY

BACKGROUND OF THE INVENTION

1. Field of the Invention

The present invention is broadly concerned with improved prostheses particularly designed for hip arthroplasties in order to securely hold the head of the femur, whether anatomical or prosthetic, thereby reducing the occurrences of dislocation of hip prostheses. More particularly, the invention pertains to a prosthesis for total hip arthroplasty comprising a metal ring constrained acetabular insert having a liner which is fixed to a person's pelvis by a shell to receive the prosthetic femur head in the liner. In preferred forms, the acetabular liner covers greater than 180° of the prosthetic femur head, and the metal ring is substantially rigid surrounding the opening of the liner to inhibit deformation of the liner and dislocation of the hip joint.

2. Description of Prior Art

To repair a hip joint, it is common to attach a shell to a patient's pelvis. A liner is typically received in the shell, and the ball or head of the femur is held in the liner. While the use of these prostheses is well established, the ball of the femur occasionally dislocates from the liner or the liner comes out of the shell. Such dislocations are debilitating and extremely painful. Some types of hip prostheses are more prone to dislocations, so that the patients must undergo additional surgery to replace or repair the prostheses. The dislocations typically occur because the liner is not securely held in the shell the liner does not engage enough of the ball of the femur, and/or the liner is too easily deformed. Thus, the force or torque required to disengage the ball of the femur from the liner, or the liner from the shell, is much less than the force or torque required to disengage the shell from the pelvis thereby permitting the ball of the femur to come out of the liner, or the liner to come out of the shell, too frequently.

SUMMARY OF THE INVENTION

The present invention overcomes the problems outlined above and provides an improved hip joint prosthesis. By virtue of a unique liner and retainer ring the improved hip joint prosthesis securely holds the ball of the femur, so that the force required to dislocate the femur ball from the liner is, by only a small predetermined amount, below the force required to separate the liner from a shell of the prosthesis. In turn, the force required to separate the liner from the shell is, by only a small predetermined amount, below the force required to separate the shell from the patient's pelvis.

Broadly speaking, the prosthesis of the present invention has a shell, a liner, and a retainer ring. The shell defines a shell receiving area for insertion of the liner therein. The liner defines a liner receiving area and a restricted liner opening to the liner receiving area. The retainer ring is continuous and substantially rigid and engages the liner and inhibit deformation of the liner.

In a preferred embodiment, an inner surface of the liner is substantially spherical and extends to envelop the circumferential side apex of the femur ball. The restricted opening of the liner has an opening diameter which is smaller than a largest diameter of the liner receiving area. The liner preferably includes an expandable portion around the restricted opening, and there are expansion slits formed in the expandable portion. The retainer ring preferably snaps to the shell with a catch leg having a plurality of contraction slots dividing the catch leg, and if desired, the retainer ring engages the liner to reduce the size of the restricted opening.

In another preferred embodiment, the catch leg includes spaced apart tabs, and the liner includes a plurality of spaced apart protrusions receiving the tabs therebetween. The shell includes recesses for receiving the protrusions and a catch ledge to engage and hold catch lips extending from lower ends of the tabs. The liner also preferably includes a plurality of liner catch lips adjacent the protrusions for engaging the catch ledge and a positioning flange for engaging the shell to form a relief gap between the shell and the liner.

In still another preferred embodiment, the retainer ring includes an attachment portion, a retainer portion, and a connection between the attachment portion and the retainer portion. The attachment portion attaches to the shell, and the retainer portion is connected to the attachment portion. The connection comprises a threaded connection in one embodiment and a snapping connection in another. With the threaded connection, the force or torque required to dislocate the femur ball can be adjusted by rotating the retainer portion to move it axially relative to the liner.

The present invention also contemplates a novel method for using the novel hip prosthesis. The shell is attached to a patient's pelvis, and the liner is inserted in the shell. The retainer ring is positioned over the patient's femur and behind the ball of the femur. The ball of the femur is forced into the liner expanding the expandable portion as the ball of the femur moves past the restricted opening of the liner. The retainer ring is attached to the shell, so that it engages the liner to inhibit expansion of the expandable portion and inhibit separation of the liner from the shell. Preferably, the liner is inserted into the shell by pushing on the positioning flanges, and the ring is snapably attached to the shell. Further, the expandable portion is preferably elastically expanded, and the retainer ring engages the liner to reduce the size of the restricted opening.

BRIEF DESCRIPTION OF THE DRAWINGS

FIG. 1 is an exploded perspective view of a hip prosthesis according to the present invention;

FIG. 2 is a vertical sectional view of the hip prosthesis of FIG. 1;

FIG. 3 is an exploded perspective view of an alternate hip prosthesis according to the present invention;

FIG. 4 is a fragmentary top view of the hip prosthesis of FIG. 3 having a portion thereof removed for illustration;

FIG. 5 is a vertical sectional view of the hip prosthesis of FIG. 3 taken along line 5—5 in FIG. 4;

FIG. 6 is a vertical sectional view of the hip prosthesis of FIG. 3 taken along line 6—6 in FIG. 4;

FIG. 7 is an exploded perspective view of another alternate hip prosthesis according to present invention;

FIG. 8 is a vertical sectional view of the hip prosthesis of FIG. 7;

FIG. 9 is an exploded perspective view of still another alternate hip prosthesis according the present invention; and FIG. 10 is a vertical sectional view of the hip prosthesis of FIG. 9.

DETAILED DESCRIPTION OF THE PREFERRED EMBODIMENTS

Turning now to the drawings, FIGS. 1 and 2 depict a hip prosthesis 20 having a shell 22, a liner 24, and a retainer ring 26. The hip prosthesis 20 shown forms an acetabular insert portion for total hip arthroplasty.

In greater detail, the substantially rigid, and preferably metal, shell 22 includes a shell wall 28 and a terminal shell margin 30. The shell wall 28 is generally cup-shaped and frustospherical having a substantially constant and spherical shell inner surface 32 defining a shell receiving area 33. An attachment opening 34 is formed in a shell base 36 of the shell wall 28. The attachment opening 34 extend through the shell wall 28 and a downwardly depending leg 35 which is integral to the shell wall. The shell wall also includes a porous coating 37. The shell wall 28 includes a circumferential catch ledge 38 having a circumferentially extending chamfer 40 on the upper corner thereof. An inwardly extending recessed region or lip receiving groove 42 extends circumferentially around the shell 22 just below the catch ledge 38. Shell wall 28 further presents a circumferential retaining wall structure opposed from catch ledge 38 which both define the upper and lower margins of groove 42.

The terminal shell margin 30 is preferably circumferential and substantially circular. The terminal shell margin 30 defines a guide ledge 44 and a guide ledge chamfer 46 between the guide ledge 44 and the upper surface 48 of the shell margin 30. The upper surface 48 is substantially flat. A perimeter rim 50 extends outwardly from the shell margin 30 increasing the surface area of the flat upper surface 48. The porous coating 37, shown in phantom, is applied between the leg 35 and the perimeter rim 50 to make the outer surface of the shell hemispherical. The terminal shell margin 30 also defines a shell opening to the shell receiving area 33. The shell opening is opposite the shell base 36.

The liner 24 includes a flexible liner wall 52 and a flexible terminal liner margin 54. The liner 24 is preferably formed from a resiliently yieldable material such as ultra high molecular weight polyethylene, but any sufficiently elastic material suitable for service as a bearing surface in an artificial joint could be used.

The liner wall 52 is generally frustospherical and has a substantially spherical inner liner surface 56 defining a liner receiving area 58. The inner liner surface 56 extends greater than 180° three-dimensionally about a geometric center of the inner surface 56. The outer surface of the liner has a spherical base portion 60 and a generally cylindrical middle portion 62.

The terminal liner margin 54 has a cylindrical outer wall 64 having a diameter greater than the diameter of the middle portion 62, so that there is a step 66 between the middle portion 62 and the outer wall 64 of the terminal liner margin 54. The terminal liner margin 54 also includes an inwardly inclined retainer rim engagement surface 68. The angled retainer ring engagement surface 68 is preferably inclined at an angle of approximately 120° with respect to the outer wall 64 of the liner margin 54. The terminal liner margin 54 also includes an outwardly inclined femur ball guide surface 70 and defines a substantially circular, restricted liner opening 72 having a diameter smaller than the largest diameter of the liner receiving area 58.

A plurality of expansion slits 74 are formed in the terminal liner margin 54, so that the terminal liner margin 54 forms an expansion portion of the liner. The expansion slits 74 open at the top of the terminal liner margin and extend into the liner 24. The expansion slits 74 may terminate with enlarged or rounded openings or simply with the rectangular configurations shown in FIGS. 1 and 2.

The retainer ring 26 includes a continuous circumferential body 76 and a circumferential catch leg 78. The body 76 of the retainer ring 26 has a rounded top 80 and a substantially flat bottom surface 82 engaging the flat upper surface 48 of the terminal shell margin 30. The retainer ring body 76 also includes an angled liner engagement surface 77 inclined at an angle of approximately 118° with respect to the outer wall of the liner 64.

The circumferential leg 78 is flexible, extends away from the bottom 82 of the retainer ring body 76, and is inwardly positioned on the bottom 82 of the retainer ring body 76 to form a snapping attachment mechanism for the retainer ring 26. Though the ring 26 preferably attaches to the shell, it could also attach to the liner, and the attachment mechanism could also be provided on the shell. The circumferential leg 78 is elongated and terminates with an outwardly extending catch lip 84. The catch leg 78 includes a plurality of open ended contraction slots 86 which open at the catch lip 84, extend into the catch leg 78, and terminate at a plurality of contraction slot bases 88. The slot bases 88 are preferably rounded and enlarged relative to the width of the contraction slots 86.

In operation, an optional fixation device (not shown) is used to attach the shell 22 to skeletal structure, preferably a patient's pelvis (not shown). Such a fixation device extends through the attachment opening 34 in the base 36 of the shell 22. The liner 24 is then inserted into the shell receiving area 33 with its arcuate base 60 abutting the arcuate, preferably spherical, shell inner surface 32. The retainer ring 26 is positioned over the patient's femur 90 (shown schematically in phantom lines) and behind the ball 92 of the femur 90. The ball 92 of the femur 90 is then forced past the expandable portion 54 of the liner 24 and guided into the liner receiving area 58 by the femur guide surface 70. By opening the expansion slits 74, the expandable liner margin 54 is elastically expanded with the ball 92, specifically the circumferential side apex 93, of the femur 90. The circumferential side apex 93 is the circumferential portion of the ball 92 the greatest distance from a central axis of the ball which is parallel to the central axis 95 of the acetabular prosthesis 20. With the femur ball 92 inside the liner receiving area 58, the retainer ring 26 is slid along the femur 90 toward the femur ball 92 until the catch leg 78 is inside the shell and the catch lip 84 is inside the lip receiving groove 42 and snapably engages the catch ledge 38 of the terminal shell wall 28. The contraction slots 86 allow the catch leg 78 to reduce in diameter as the catch lip 84 slides over the chamfer 40 of the catch ledge 38, and the enlarged slot bases 88 inhibit stress build up which might damage the retainer ring 26. The guide ledge 44 and guide ledge chamfer 46 further expedite alignment of the catch leg 78 in the shell 22.

With the retainer ring snapped in place, the liner engagement surface 77 engages the retainer ring engagement surface 68 and the outer wall 64 of the liner margin 54. Because the angle of the liner engagement surface 77 on the retainer ring is less than the angle of the retainer ring engagement surface 68 of the liner, the retainer ring reduces the size of the restricted opening 72. In this embodiment, the femur lead should be configured to permit constriction of the restricted opening 72.

The rigid retainer ring 26 inhibits the expandable liner margin 54 from expanding and the liner covers greater than 180° of the femur ball 92 to hold the femur ball 92 inside the liner. That is, the liner extends to envelop greater than a hemisphere of the ball. If the ball is not spherical, the liner can be described as extending to envelop the side apex 93 of the ball or envelop greater than 50% of the outer surface or the volume of the femur ball 92. Thus, the metal retainer ring 26 constrains the acetabular insert and keeps the side apex 93 of the femur ball 92 from sliding out of the liner.

Because the restricted liner opening 72 cannot significantly expand, the femur ball 92 is securely held in the liner. Preferably, the torque or force required to dislocate the femur ball from the liner is just below the torque or force required to separate the liner from the shell and the force required to separate the liner from the shell is just below the force or torque required to separate the shell 22 from the patient's pelvis. Therefore, the present design significantly reduces the occurrences of prosthetic hip dislocations while permitting dislocations when necessary to protect the pelvis from fracture.

Referring to FIG. 3, an alternate metal ring constrained acetabular insert 94 also includes a shell 96, liner 98, and retainer ring 100. This alternate hip prosthesis 94 and its function will be described only to the extent that they are unique from the previously described embodiment of FIGS. 1 and 2. Further, similar reference numerals will be used on similar components and differentiated by the suffix A.

Referring additionally to FIGS. 4, 5, and 6, the shell 96 includes a plurality of recesses 102, preferably twelve, evenly spaced around the circumference of the terminal liner margin 54A. The recesses 102 are arcuate, preferably portions of a circle, and are positioned above the catch ledge 38A. The recesses 102 also include recess guide chamfers 104 adjacent the upper surface 48A of the shell margin 54A.

The liner 98 includes a plurality of protrusions 106, a plurality of liner catch lips 108, and a plurality of positioning flanges 110. The protrusions 106 are rounded, each preferably including a portion of a circle, and are positioned between the liner catch lips 108 and the positioning flanges 110. The liner catch lips are flexible and are positioned at the intersection of the base portion 60A and the circumferential middle portion 62A of the liner 98. The positioning flanges 110 are positioned above the protrusions 106 and include a substantially flat underside 112 which engages the flat upper surface 48A of the shell 96.

The protrusions 106, liner catch lips 108, and positioning flanges 110 are provided in six groups, each group having one of each, evenly spaced-apart by constant radius areas, around the circumference of the middle portion 62A of the liner. The expansion slits 74A are centrally positioned above the spaced-apart groups of protrusions, flanges, and liner catch lips. The liner also includes an inwardly inclined retainer ring engagement surface 68A which is angled at approximately 170° with respect to the cylindrical wall of the middle portion 62A.

The retainer ring 100 includes a intermittent catch leg 114 (FIG. 3) having a plurality of tabs 116 with tab catch lips 118 at lower ends of the tabs 116. The tabs are evenly spaced-apart to fit between the spaced-apart positioning flanges 110. The liner engagement surface 77A of the retainer ring has an angle of 168°.

In operation, the liner 98 is pushed into the shell 96 by applying force to the positioning flanges 110. The liner is pushed into the shell 96 until the liner catch lips 108 extend into the lip receiving groove 42A and are engaged by the catch ledge 38A of the shell 96. Because there are more recesses than protrusions, preferably twice as many, the liner protrusions 106 are easily aligned with a set of six recesses 102. The undersides 112 of the positioning flanges 110 engage the upper surface 48A of the shell margin 54A leaving a relief gap 120 between the base 60A of the liner and the base 36A of the shell 96. The catch legs of the retainer ring 100 are then aligned between the positioning flanges 106 and pushed into the shell until the tab catch lips 118 extend into the confines of and snap into the lip receiving groove 42A.

The protrusions 106 extend into the recesses 102 and are guided therein by the recess guide chamfers 104. With the protrusions 106 in the recesses 102, rotation of the liner 98 relative to the shell 96 is inhibited. As the femur ball 92 is pushed further into the liner 98 during in-vivo use, the liner deforms as permitted by the relief gap 120 thus cushioning relative movement between the femur ball 92 and the shell 96.

Referring to FIGS. 7 and 8, another alternate hip prosthesis 122 also includes a shell 124, liner 126, and retainer ring 128, 130. This alternate hip prosthesis 122 and its function will be described only to the extent that they are unique from the previously described embodiment of FIGS. 1 and 2. Further, similar reference numerals will be used on similar components and differentiated by the suffix B.

The shell 124 is substantially identical to the shell shown in FIGS. 1 and 2. The liner 126 is also substantially the same as the liner of FIGS. 1 and 2, but the middle portion 62B of the liner has substantially the same diameter as the outer wall 64B of the liner margin 54B.

The retainer ring includes an attachment portion 128 and a retainer portion 130. A threaded connection 132 is formed between the attachment portion 128 and the retainer portion 130. The retainer ring includes the catch leg 78B and the catch lip 84B, and the retainer ring further includes a liner engagement protrusion 134 opposite the catch lip 84B.

In operation, the retainer portion 130 of the retainer ring is positioned as described on the patient's femur, and the attachment portion 128 is snapped in the shell. Specifically, the catch lip 84B is snapped into the lip receiving groove 42B. After the femur ball is inserted in the liner 126, the liner is inserted in the shell and attachment portion, and the attachment portion 128 is snapped into the shell. The increased diameter of the middle portion 62A and the protrusion 134 engage each other and force the catch lip 84B into a more secure engagement with the catch ledge 38B and grip the liner to inhibit rotation of the liner.

The retainer portion 130 is then threaded onto the attachment portion 128 until the liner engagement surface 77B engages the retainer ring engagement surface 68B of the liner 126. By further threading the retainer portion 130 onto the attachment portion 128, the retainer portion moves axially closer to the shell, the liner margin 54B is compressed, and the restricted liner opening 72B is thereby further restricted. Specifically, the diameter of the liner opening is reduced by closing the expansion slits 74B. In this manner, a physician can adjust the force or torque required to dislocate the femur ball from the liner.

Referring to FIGS. 9 and 10, still another alternate hip prosthesis 136 also includes a shell 138, liner 140, and retainer ring 142, 144. This alternate hip prosthesis 136 and its function will be described only to the extent that they are unique from the previously described embodiments of FIGS. 1, 2, 7, and 8. Further, similar reference numerals will be used on similar components and differentiated by the suffix C.

The retainer ring includes an attachment portion 142 and a retainer portion 144. The attachment portion 142 includes an upwardly extending alignment tab 146 and a outwardly facing hook 148 having a downwardly inclined surface 149.

The retainer portion includes a hook leg 150 having an inwardly extending snap hook 152 at the lower end of the hook leg 150. The snap hook 152 includes an inclined lower, inner surface 158. The hook leg is circumferential and includes a plurality of hook expansion slits 154 spaced around the circumference of the hook leg 150. The hook leg 150 is outwardly positioned on the retainer portion 144. The retainer portion 144 also includes an alignment groove 156.

In operation, the attachment portion 142 is snapped into the shell 138, and the retainer portion 144 is pushed onto the attachment portion 142. The inclined surface 158 of the snap hook 152 slides over the inclined surface 149 of the hook 148 until the snap hook 152 engages the hook 148 thereby attaching the retainer portion 144 to the attachment portion 142 and inserting the alignment tab 146 into the alignment groove 156 to fix the retainer portion relative to the attachment portion. As the inclined surface 158 of the snap hook 152 slides past the inclined surface 149 of the hook 148, the expansion slits 154 open allowing the hook leg to increase in diameter.

The above described hip prosthesis in its various embodiments provides significant advantages over prior art prostheses. The disclosed prostheses securely holds the femur head to reduce the occurrences of dislocation thereby increasing the desirability, longevity, and usefulness of hip prostheses.

We claim:

1. A prosthesis comprising:
    a substantially rigid shell for attachment to skeletal structure, the shell including a shell wall defining a shell receiving area and a terminal shell margin defining a shell opening to the shell receiving area, the shell wall including an inwardly extending recessed region presenting a circumferential catch ledge proximal to said shell margin;
    a resiliently yieldable liner for insertion in the shell receiving area, the liner including a liner wall having a liner inner surface defining a liner receiving area, the liner wall having a terminal liner margin defining a restricted liner opening to the receiving area; and
    a substantially rigid retainer ring presenting an axially extending catch leg having a catch lip extending outwardly from the catch leg,
    upon assembly of the prosthesis, the ring engaging the liner wall to inhibit deformation thereof and the catch lip extending into the confines of said recessed region and engaging the catch ledge to secure the liner in the shell receiving area.

2. The prosthesis according to claim 1 wherein the liner extends to envelop a circumferential side apex of a femur ball.

3. The prosthesis according to claim 1 wherein the inner surface is substantially spherical, and the liner extends to envelop greater than a hemisphere of a femur ball.

4. The prosthesis according to claim 1 wherein the restricted liner opening has a liner opening diameter smaller than a largest diameter of the liner receiving area.

5. The prosthesis according to claim 1 wherein the liner comprises a plurality of expansion slits positioned adjacent the terminal liner margin and extending into the liner whereby the restricted liner opening is enlargable and can be further restricted.

6. The prosthesis according to claim 1 wherein the catch leg and catch ledge form a snapping attachment mechanism attaching the retainer ring to the shell.

7. The prosthesis according to claim 1 wherein the catch leg includes a plurality of contraction slots dividing the catch leg.

8. The prosthesis according to claim 1 wherein the retainer ring includes an angled liner engagement surface, the liner includes an angled retainer ring engagement surface, and a liner engagement surface angle is less than a retainer ring engagement surface angle.

9. The prosthesis according to claim 8 wherein the liner engagement surface angle is approximately 168°, and the retainer ring engagement surface angle is approximately 170°.

10. The prosthesis according to claim 1 wherein the catch leg comprises an intermittent catch leg including spaced apart tabs, the protrusions are spaced apart to receive the tabs therebetween, and there are more recesses than protrusions.

11. The prosthesis according to claim 1 wherein the liner inner surface extends greater than 180° three dimensionally about a geometric center of the inner surface.

12. The prosthesis according to claim 1 where the liner includes a liner catch lip, the shell catch ledge engaging and holding the liner catch lip.

13. The prosthesis according to claim 1 wherein the retainer ring comprises an attachment portion having the attachment mechanism thereon, a retainer portion engaging the terminal liner edge, and a connection between the attachment portion and the retainer portion.

14. The prosthesis according to claim 1 wherein the liner includes a positioning flange for engaging an upper surface of the terminal shell margin forming a relief gap between the shell and the liner.

15. A hip prosthesis comprising:
    a substantially rigid shell for attachment to a pelvis, the shell including a shell wall defining a shell receiving area and a terminal shell margin defining a shell opening to the shell receiving area, the shell wall including a circumferential recessed region presenting a catch ledge proximal to said shell margin;
    a resiliently yieldable liner for insertion in the shell receiving area, the liner including a liner wall having a liner inner surface defining a liner receiving area, an expandable terminal liner margin defining a restricted liner opening to the receiving area, and a base portion opposite the terminal liner margin; and
    a unitary, continuous and substantially rigid retainer ring presenting an axially extending catch leg having a catch lip extending outwardly from the catch leg and into the confines of said recessed region,
    upon assembly of the prosthesis, the ring engaging the liner wall to inhibit expansion thereof and die catch lip extending into the confines of said recessed region and engaging the catch ledge to secure the liner in the shell receiving area.

16. The hip prosthesis according to claim 15 wherein the expandable liner margin comprises a plurality of expansion slits.

17. A method for hip arthroplasty, the method comprising:
    attaching a shell to a patient's pelvis, the shell including a shell wall presenting a terminal shell margin and a recessed region including a circumferential catch ledge proximal to said shell margin;
    inserting a liner having an expandable portion into the shell;
    positioning a retainer ring over the patient's femur and behind a ball of the femur, said retainer ring presenting an axially extending catch leg and a catch lip extending outwardly from the catch leg;
    expanding the expandable portion of the liner with the ball of the femur;
    forcing the ball of the femur past the expandable portion and into the liner;
    attaching the retainer ring to the shell thereby causing the ring catch lip to extend into the confines of said recessed region and engage the shell catch ledge; and engaging the expandable portion of the liner with the retainer ring to inhibit expansion of the expandable portion of the liner.

18. The method according to claim 17 wherein attaching the retainer ring comprises snapping the retainer ring to the shell, and expanding the expandable portion of the liner comprises elastically expanding the expandable portion of the liner.

19. The method according to claim 17 wherein positioning the retainer ring over the femur comprises positioning a retainer portion of the retainer ring over the femur, and attaching the retainer ring comprises attaching the attachment portion to the shell and connecting the retainer portion to the attachment portion.

20. The method according to claim 17 further comprising forming a relief gap between a base of the shell and a base of the liner.

21. The prosthesis according to claim 1 wherein said shell wall presents a circumferential retaining wall structure opposed from said catch ledge, said retaining wall structure and said catch ledge defining the upper and lower margins of said shell wall recessed region.

* * * * *